(12) United States Patent
Fröhlich et al.

(10) Patent No.: US 8,667,612 B2
(45) Date of Patent: Mar. 11, 2014

(54) EYE PROTECTION CAP

(75) Inventors: Thomas Fröhlich, Lauf a. d. Pegnitz (DE); Peter Bura, Aichwald (DE)

(73) Assignee: Laservision GmbH & Co. KG, Fuerth (DE)

( * ) Notice: Subject to any disclaimer, the term of this patent is extended or adjusted under 35 U.S.C. 154(b) by 356 days.

(21) Appl. No.: 12/831,511

(22) Filed: Jul. 7, 2010

(65) Prior Publication Data
US 2011/0004969 A1    Jan. 13, 2011

(30) Foreign Application Priority Data

Jul. 7, 2009    (DE) .......................... 10 2009 032 178

(51) Int. Cl.
*A61F 9/00*    (2006.01)
(52) U.S. Cl.
USPC .............................. 2/15; 2/426; 2/434; 2/440
(58) Field of Classification Search
USPC ............... 2/9, 11, 12, 15, 439, 440, 432, 426, 2/431, 428, 442, 436; 128/857, 858, 846, 128/853; 351/44, 47, 63, 41, 158, 45, 46, 351/110, 43; 604/301, 302, 303, 307, 294, 604/295; 428/156; 602/72, 74; D16/300–302, 305–308
See application file for complete search history.

(56) References Cited

U.S. PATENT DOCUMENTS

| 4,570,626 A | | 2/1986 | Norris et al. |
| 4,655,767 A | | 4/1987 | Woodard et al. |
| 5,004,333 A | * | 4/1991 | Bruhl, Jr. ........................ 351/45 |
| 5,524,642 A | * | 6/1996 | Rosenblatt ................... 128/849 |
| 5,970,515 A | | 10/1999 | Fishbaugh |
| 6,123,081 A | | 9/2000 | Durette |
| RE39,896 E | * | 10/2007 | Arnold et al. ................... 602/54 |
| 2008/0148461 A1 | * | 6/2008 | Guyuron et al. .................... 2/15 |

FOREIGN PATENT DOCUMENTS

| DE | 69913455 T2 | 10/2004 |
| DE | 69919808 T2 | 9/2005 |
| DE | 10 2005 058 888 B3 | 3/2007 |
| DE | 602005001326 | 2/2008 |
| EP | 998 887 B1 | 9/2004 |
| EP | 1562067 A1 | 8/2005 |
| WO | 94/15557 A2 | 7/1994 |

* cited by examiner

*Primary Examiner* — Khoa Huynh
*Assistant Examiner* — Khaled Annis
(74) *Attorney, Agent, or Firm* — Browdy and Neimark, PLLC

(57) ABSTRACT

The invention relates to an eye protection cap to protect an eye of a person to be treated against electromagnetic radiation, in particular against laser radiation. The eye protection cap comprises a dimensionally stable shaped body, which has a free edge for adjacent arrangement in relation to the person to be treated, limits a hollow shaped body interior, is formed from a silicone material and has a self-holding region for independent holding on the person to be treated.

14 Claims, 4 Drawing Sheets

EYE PROTECTION CAP

FIELD OF THE INVENTION

The invention relates to an eye protection cap to protect an eye of a person to be treated against electromagnetic radiation, in particular against laser radiation.

BACKGROUND OF THE INVENTION

Wrinkles or skin anomalies such as age spots and warts can be treated in people by medical laser treatments. In this case, the eyes of the person to be treated and the eyes of the person who is treating have to be protected against the laser radiation occurring.

To protect the eyes of the person to be treated, known eyeball spectacles can be used, for example, which comprise two half shells to cover the eyes. The half shells are connected to one another by a nose bridge and are held by means of a headband on the head of the person to be treated. The headband and the nose bridge restrict access to the regions around the eye, in particular in laser treatments in the dermatological and cosmetics areas. A treatment in these regions can only take place if the headband and/or the nose bridge are removed or locally offset. The person to be treated is then exposed to an increased risk from the laser. Generic eyeball spectacles are known, for example, from DE 10 2005 058 888 B3.

Furthermore, self-adhesive eye pads are known, which are to be stuck to the eye of the person to be treated. These eye pads allow good access to the entire regions around the eye of the person to be treated as no headbands and nose bridges are provided for fixing. The laser protection effect of the eye pads is very small due to the structure. It is also disadvantageous that the eye pads are disposable articles.

Contact lenses made of metal are also often inserted to protect the person to be treated. Although these do offer extremely high laser protection, they are very unpleasant for the person to be treated to wear. These contact lenses are substantially only used when the eyelid of the person to be treated is to be treated.

SUMMARY OF THE INVENTION

The invention is based on the object of providing an eye protection cap, which on the one hand, provides extremely high protection against electromagnetic radiation and, on the other hand, offers good access for a person who is treating to regions around the eye of a person to be treated. Furthermore, the eye protection cap should be comfortable to wear for the person to be treated.

This object is achieved according to the invention by an eye protection cap comprising a dimensionally stable shaped body having a free edge for adjacent arrangement in relation to the person to be treated, and limiting a hollow shaped body interior, and being formed from a silicone material, and having a self-holding region for independent holding on the person to be treated.

The core of the invention is that the eye protection cap has a hollow silicone shaped body, which can be attached in a self-holding manner to the person to be treated. Separate holding means such as headbands, nose bridges or the like are therefore not required. The shaped body is dimensionally stable. However, it may also be flexible to a certain extent or be variable with respect to its shape. The shape of the shaped body can, however, in particular, not be permanently changed during proper use of the eye protection cap.

A preferred embodiment of the invention will be described below with reference to the accompanying drawings.

DESCRIPTION OF THE PREFERRED EMBODIMENT

Figure 1:
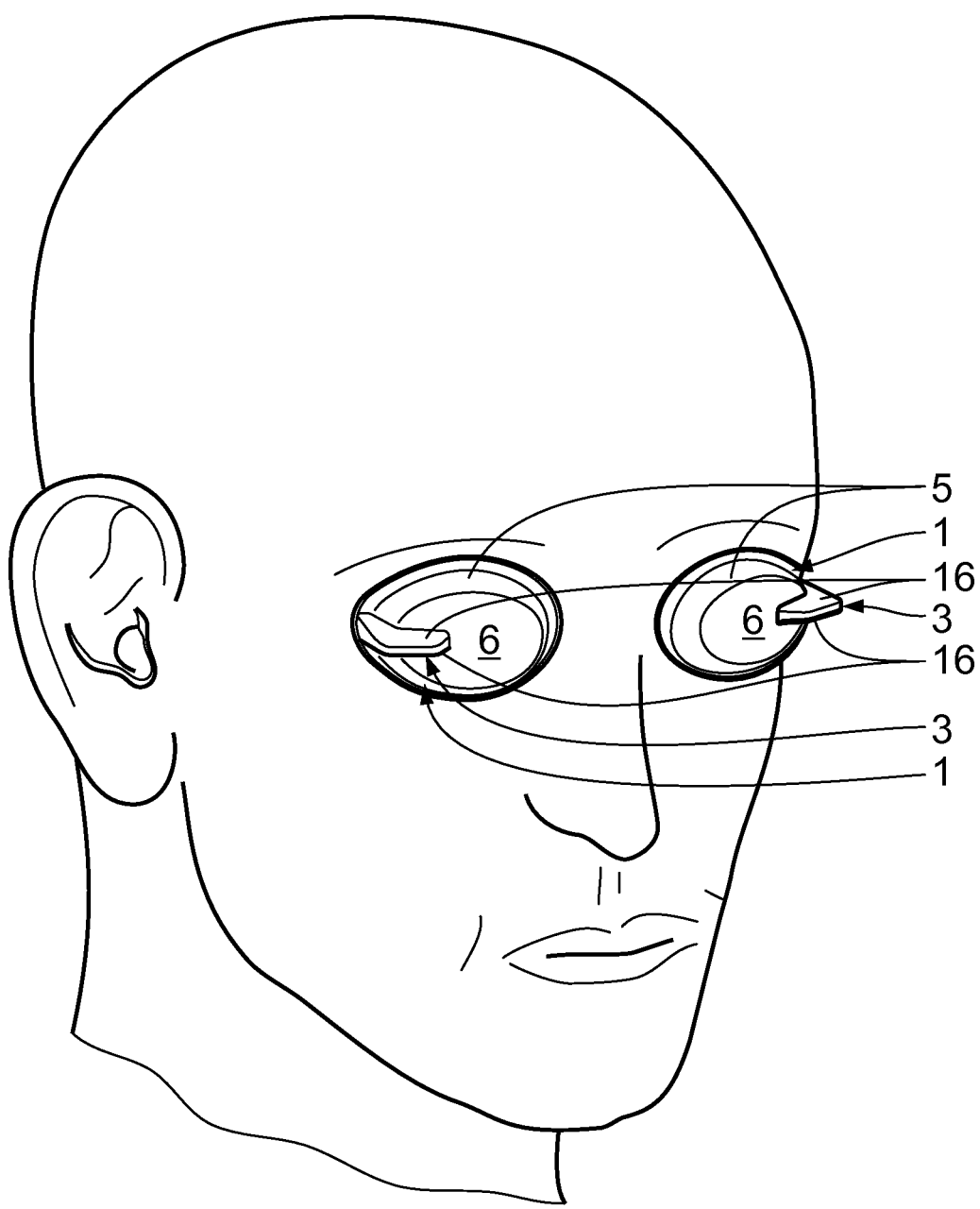
FIG. 1 shows a head of a person to be treated, who is wearing two eye protection caps according to the invention.
Figure 2:
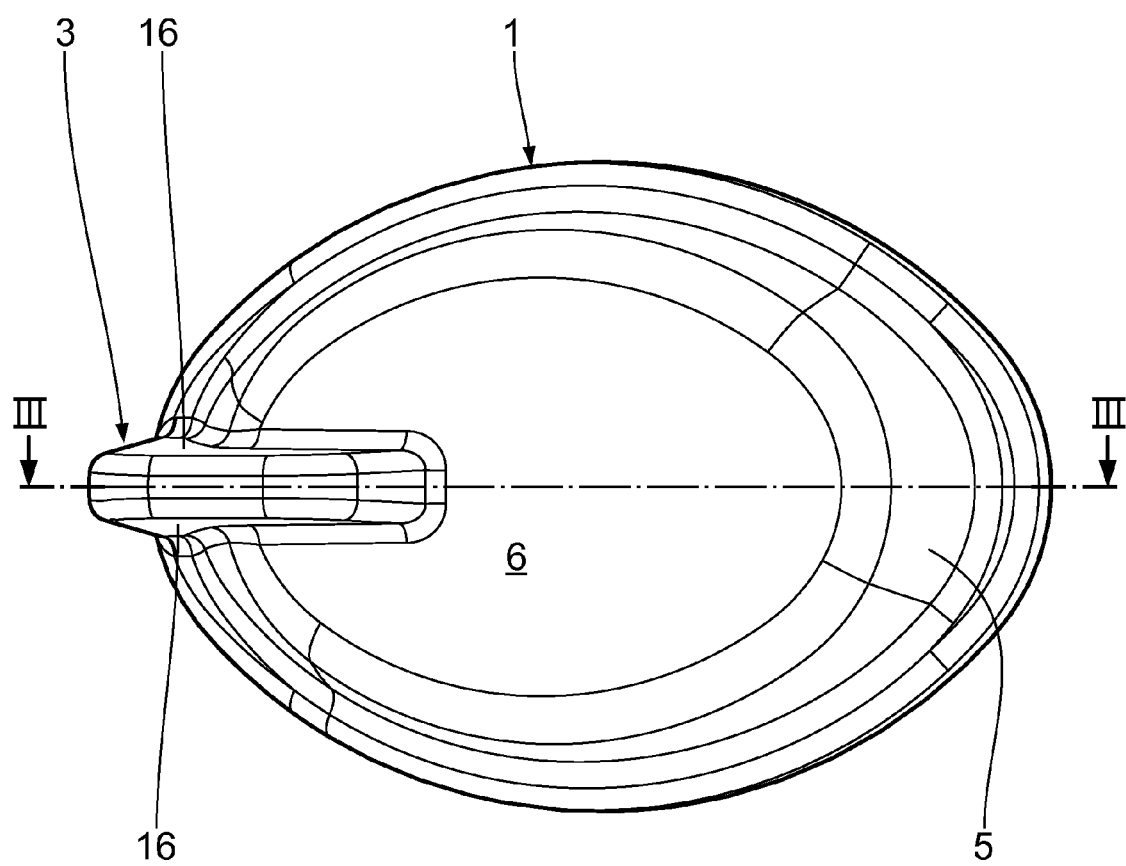
FIG. 2 shows a plan view of an eye protection cap according to the invention, shown in FIG. 1.
Figure 3:
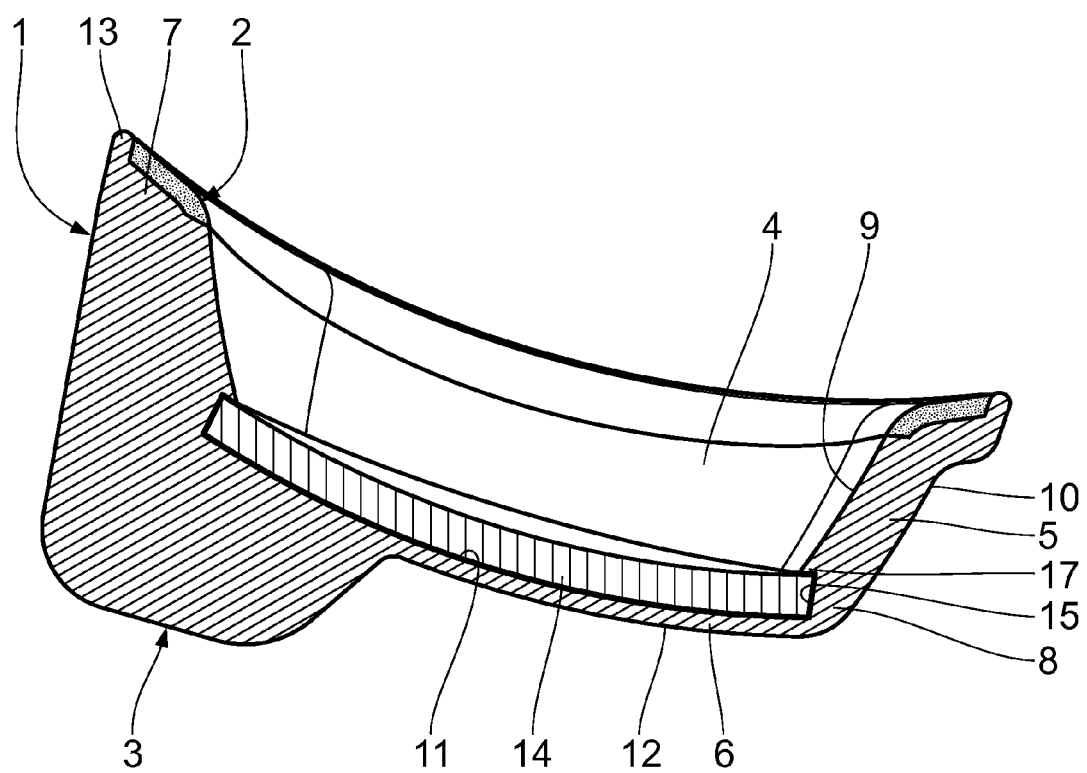
FIG. 3 shows a section though the eye protection cap shown in FIG. 2 along the section line III-III.
Figure 4:
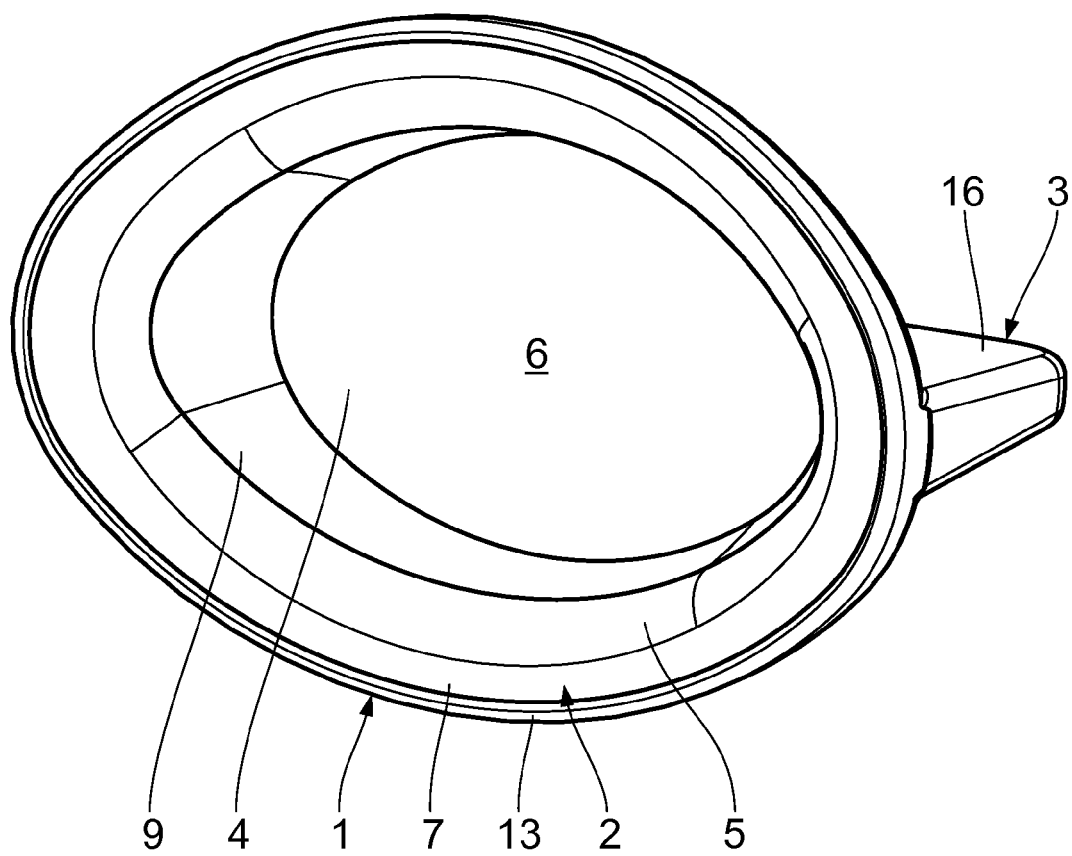
FIG. 4 shows a view which shows an eye protection cap shown in FIGS. 1 to 3 from behind.

An eye protection cap for protecting an eye of a person to be treated against electromagnetic radiation, in particular against laser radiation, comprises a one-piece, hollow shaped body 1, a self-holding region 2 for independent holding of the shaped body 1 on the person to be treated and a handling handle 3. The shaped body 1 is made of a silicone material with a hardness of, in particular, at least 50 Shore A and preferably of 60 Shore A and outwardly limits a hollow shaped body interior 4. The eye protection cap is provided for use in medical or cosmetic laser treatments.

The shaped body 1, which is formed from a silicone material, is configured in a shell-like manner and has an extended basic shape. Owing to the extended basic shape, the shaped body interior 4 is substantially oval in cross section. The shaped body 1 has a peripheral, closed side wall 5 and a substantially level cover 6, which is connected at the edge to the side wall 5 and is slightly convexly curved in relation to the shaped body interior 4. The side wall 5 extends transversely to the cover 6. The side wall 5 and the cover 6 are configured in one-piece, the cover being a solid piece that extends over the entire region enclosed by said side wall, and said side wall and said cover being constructed to effectively block radiation.

The side wall 5 has a free foot edge 7, which is opposite a head region 8 of the side wall 5 and also projects laterally outwardly from the side wall 5. The foot edge 7 extends in such a way that upon application of the eye protection cap, it surrounds an eye or an eye socket of the person to be treated. In the head region 8 of the side wall 5, which is spaced apart from the foot edge 7, the cover 6 adjoins the side wall 5. The side wall 5 has a substantially constant height and tapers over its height proceeding from its foot edge 7 in the direction of its head region 8, so ultimately the shaped body interior 4 also uniformly tapers from the foot edge 7 of the side wall 5 to the head region 8 of the side wall 5. The shaped body interior 4 is laterally limited by the side wall 5 and upwardly limited by the cover 6. At the foot edge 7, the shaped body interior 4 is outwardly open or accessible.

Furthermore, the side wall 5 has an inner region 9 which faces inward and an outer region 10 opposing this. The cover 6 also has an inner region 11 and an outer region 12 facing outward. The shaped body interior 4 is limited by the inner region 9 of the side wall 5 and by the inner region 11 of the cover 6.

Provided at the foot edge 7, is the self-holding region 2, which also consists of a silicone material and is configured in a layer-like manner. The self-holding region 2 extends at the foot edge 7 over the entire periphery of the side wall 5, so the self-holding region 2 is peripherally closed. Although the shaped body 1 and the self-holding region 2 are made from the same basic material, namely, in particular, silicone, the silicone material of the self-holding region 2 differs from the silicone material of the shaped body 1. It is substantially softer than the silicone material of the shaped body 1 and has a hardness of, in particular, at most 10 Shore A, preferably of about 0 Shore A. Because of the construction from the same basic material, the shaped body 1 and the self-holding region 2 are connected to one another particularly well and, in particular, intimately. The self-holding region 2 is also very self-adhesive, so the eye protection cap can be fixed to the eye area of the patient purely by means of adhesive force. The self-holding region 2 is limited laterally outwardly by a web or bridge 13, which projects downwardly from the side wall 5. The height of the bridge 13 approximately corresponds to the thickness of the self-holding region 2. The self-holding region 2 continues into the shaped body interior 4, so the self-holding region 2 extends in a curved manner at least in regions over its width.

Inserted into the shaped body 1 on the inside, is an additional protection element 14, which can also protect against electromagnetic radiation, in particular against laser radiation. It has a curvature adapted to the cover 6 so it abuts on the inside of the cover 6 over the entire inner region 11. The additional protection element 14 and the cover 6 extend substantially in mutually parallel areas. The additional protection element 14 is configured as a small oval metal plate here and virtually forms a further cover. The additional protection element 14 is thicker than the cover 6. It is rigid. In particular, the small metal plate consists of aluminium. Other suitable materials may also be used.

For local, but also for releasable fixing of the additional protection element 14 in the shaped body 1, a groove-like holding recess 15 is provided in the inner region 9 of the side wall 5 in the head region 8 thereof, said holding recess being configured peripherally and open toward the shaped body interior 4. The height of the holding recess 15 approximately corresponds to the thickness of the additional protection element 14. The additional protection element 14 can be locally fixed by the holding recess 15 in the shaped body interior 4, resting on the cover 6. The additional protection element 14 can also be removed again. The holding recess 15 and the additional protection element 14 are adapted to one another with regard to shape and size. The additional protection element 14 may, however, also be fixed in a different manner. For example, it may also be fixed to the cover 6 by means of a plurality of holding recesses, latching lugs or by means of a clamping or by means of static friction to the inner region 9 of the side wall 5.

The handling handle 3 is connected in one piece to the shaped body 1 and is formed from the same silicone material as the shaped body 1. It is configured as a projection, which projects laterally outwardly from the outer region 10 of the side wall 5 and projects upwardly from the outer region 12 of the cover 6. The handling handle 3 has two mutually opposing handle faces 16. The eye protection cap is symmetrical with regard to a plane of symmetry, which passes centrally through the handling handle 3.

The placing and the use of the eye protection cap will be described below in more detail. As can be seen from FIG. 1, the two eye protection caps completely cover the two eyes of the person to be treated. Only the head of the person to be treated is shown. Each eye is provided with its own eye protection cap. Since the eye protection caps are configured identically, only one eye protection cap will be dealt with. The self-holding region 2 of the eye protection cap runs around the eye or the eyeball of the person to be treated and rests closely on the facial regions adjacent to the eye of the person to be treated. Because of the adhesive effect of the self-holding region 2, the shaped body 1 is held there securely without further auxiliary means. Because of the resilient configuration of the self-holding region 2 and of the shaped body 1, which can also be deformed to a certain extent, the eye protection cap can be precisely adapted to the respective person to be treated and rest closely on the face of the person to be treated. Anatomical differences in the people to be treated can thereby be compensated. The shaped body interior 4 is located directly over the eye of the person to be treated. It is open toward the eye of the person to be treated. Owing to the side wall 5, the cover 6 extends at a spacing from the eye of the person to be treated, so the person to be treated can open and close their covered eye even during the treatment. The eyelashes of the person to be treated do not touch the eye protection cap. This increases the wearing comfort.

The eye protection cap can be removed by the handling handle 3 from the person to be treated, or be placed on the eye of the person to be treated. In this case, the eye protection cap is to be held by the handle faces 16.

The additional protection element 14 can be inserted into the shaped body 1 before use from the foot edge 7. It is to be pressed manually from below into the holding recess 15, in which it then engages and is securely held. In the direction of the foot edge 7, the additional protection element 14 is secured by a web-like holding lip 17, which projects inwardly from the inner region 9 of the side wall 5 into the shaped body interior 4 and extends over the entire periphery of the side wall 5. The holding lip 17 is connected in one-piece to the shaped body 1 and engages under the additional protection element 14 at the edge. When inserting the additional protection element 14, the additional protection element 14 is to be pressed over the holding lip 17. The protection against laser radiation can be further increased by the additional protection element 14.

The eye protection cap and optionally also the additional protection element 14 reliably prevent laser radiation, during a laser treatment, being able to arrive in the shaped body interior 4 or at the covered eye of the person to be treated. No laser radiation can arrive in the shaped body interior 4 or at the covered eye of the person to be treated from the foot edge 7 either.

Because of the high adhesive effect of the self-holding region 2, no additional holding means are required, such as, for example, nose bridges, which otherwise connect conventional eye protection caps to one another. Other auxiliary means, which hold the eye protection caps on the head of the wearer, are also superfluous. According to the prior art, conventional side pieces or headbands are usually used for this. The person who is treating, such as a doctor or a beautician, can thus, easily and without problems, reach all the facial regions, which are directly adjacent to the foot edge 7.

The eye protection cap can be sterilised by steam, for example. It can therefore be used again. The eye protection cap is moreover also extremely thermally stable, which is to be attributed to the silicone configuration of the shaped body 1 and the self-holding region 2.

What is claimed is:

1. An eye protection cap to protect an eye of a person to be treated against electromagnetic radiation, wherein the eye protection cap comprises a dimensionally stable cup-shaped body,
   a) which has a free edge for adjacent arrangement in relation to the person to be treated,
   b) which has a cup-shaped wall that defines a hollow shaped body interior, the cup-shaped wall comprising a circumferential side wall and a cover connected to the side wall, the entirety of said cover being a solid piece that extends over the entire region enclosed by said side wall, and said side wall and the entirety of said cover being constructed to effectively block radiation,
c) which is formed from a silicone material, and
d) which has a self-holding region for independent holding on the person to be treated,
e) wherein at least one holding recess is defined in the side wall of the cup-shaped body for insertion of an additional protection element, the at least one holding recess being provided adjacent to the cover so that the additional protection element is in direct contact with the cover and spaced from the free edge,
f) wherein, during use of the eye protection cap, the hollow shaped body interior is located directly over the eye of the person to be treated and is open toward the eye of the person to be treated, wherein the person to be treated can open and close their covered eye during the treatment even when the additional protection element is inserted in the recess, wherein the eye lashes of the person to be treated do not touch the eye protection cap.

2. An eye protection cap according to claim 1 to protect an eye of a person to be treated against laser radiation.

3. An eye protection cap according to claim 1, wherein the free edge is formed on the side wall.

4. An eye protection cap according to claim 3, wherein the self-holding region is provided on the free edge of the side wall.

5. An eye protection cap according to claim 1, wherein the self-holding region is self-adhesive.

6. An eye protection cap according to claim 1, wherein the self-holding region is formed by a flexible silicone material.

7. An eye protection cap according to claim 6, wherein the silicone material of the self-holding region is softer than the silicone material of the shaped body.

8. An eye protection cap according to claim 1, wherein the self-holding region is peripherally closed.

9. An eye protection cap according to claim 1, in combination with the additional protection element (14), and wherein said additional protection element is a small metal plate.

10. An eye protection cap according to claim 1, wherein the additional protection element extends over at least a large part of the cover.

11. An eye protection cap according to claim 1, wherein the additional protection element is releasably inserted in the shaped body interior.

12. An eye protection cap according to claim 1, wherein the additional protection element is fastened to the cup-shaped body by means of the at least one holding recess.

13. An eye protection cap according to claim 1, comprising a handling handle which is attached to the cup-shaped body.

14. An eye protection cap to protect an eye of a person to be treated against electromagnetic radiation, wherein the eye protection cap comprises a dimensionally stable cup-shaped body,
a) which has a free edge for adjacent arrangement in relation to the person to be treated,
b) which has a cup-shaped wall that defines a hollow shaped body interior, the cup-shaped wall comprising a circumferential side wall and a cover connected to the side wall, the entirety of said cover being a solid piece that extends over the entire region enclosed by said side wall, and said side wall and the entirety of said cover being constructed to effectively block radiation,
c) which is formed from a silicone material, and
d) which has a self-holding region for independent holding on the person to be treated,
e) wherein at least one holding recess is defined in the side wall of the cup-shaped body for insertion of an additional protection element, the at least one holding recess being provided adjacent to the cover so that the additional protection element is in direct contact with the cover and spaced from the free edge,
f) wherein, during use of the eye protection cap, the shaped body interior is located directly over the eye of the person to be treated and is open toward the eye of the person to be treated, wherein the person to be treated can open and close their covered eye during the treatment even when the additional protection element is arranged in the shaped body, wherein the eye lashes of the person to be treated do not touch the eye protection cap, wherein the additional protection element is fastened to the shaped body by means of the at least one holding recess.

* * * * *